United States Patent
Arkles et al.

(10) Patent No.: US 12,171,863 B2
(45) Date of Patent: Dec. 24, 2024

(54) COMPOSITIONS AND METHODS FOR RESHAPING KERATIN-RICH SUBSTRATES AND FORMING ADHERENT FLEXIBLE FILMS

(71) Applicant: Gelest, Inc., Morrisville, PA (US)

(72) Inventors: Barry C. Arkles, Pipersville, PA (US); Jonathan D. Goff, Philadelphia, PA (US); Alison Anne Phillips, Feasterville, PA (US); Kerry Campbell Demella, Philadelphia, PA (US)

(73) Assignee: GELEST, INC., Morrisville, PA (US)

( * ) Notice: Subject to any disclaimer, the term of this patent is extended or adjusted under 35 U.S.C. 154(b) by 0 days.

(21) Appl. No.: 17/570,437

(22) Filed: Jan. 7, 2022

(65) Prior Publication Data
US 2022/0125704 A1    Apr. 28, 2022

Related U.S. Application Data

(62) Division of application No. 16/812,700, filed on Mar. 9, 2020, now Pat. No. 11,318,083.

(60) Provisional application No. 62/838,691, filed on Apr. 25, 2019.

(51) Int. Cl.
| | |
|---|---|
| *A61K 8/892* | (2006.01) |
| *A61K 8/362* | (2006.01) |
| *A61K 8/41* | (2006.01) |
| *A61K 8/58* | (2006.01) |
| *A61Q 5/00* | (2006.01) |
| *A61Q 5/06* | (2006.01) |

(52) U.S. Cl.
CPC .............. *A61K 8/892* (2013.01); *A61K 8/362* (2013.01); *A61K 8/41* (2013.01); *A61K 8/585* (2013.01); *A61Q 5/002* (2013.01); *A61Q 5/06* (2013.01)

(58) Field of Classification Search
CPC .......... A61K 8/362; A61K 8/41; A61K 8/585; A61K 8/892; A61K 8/25; A61K 8/42; A61K 8/898; A61K 2800/95; A61Q 5/002; A61Q 5/06; A61Q 5/00
See application file for complete search history.

(56) References Cited

U.S. PATENT DOCUMENTS

| | | | |
|---|---|---|---|
| 3,951,156 A | | 4/1976 | Gadzala et al. |
| 4,720,383 A | | 1/1988 | Drach et al. |
| 6,001,378 A | † | 12/1999 | Desjonqueres |
| 6,116,250 A | † | 9/2000 | Buheitel |
| 6,306,377 B1 | | 10/2001 | Coppola et al. |
| 7,682,622 B2 | † | 3/2010 | Horino |
| 9,713,583 B1 | † | 7/2017 | Pressly |
| 2004/0202637 A1 | | 10/2004 | Yoshioka et al. |
| 2013/0192624 A1 | | 8/2013 | Florence et al. |
| 2014/0193500 A1 | † | 7/2014 | Cotrell |
| 2015/0034117 A1 | † | 2/2015 | Pressly |
| 2015/0328102 A1 | † | 11/2015 | Pressly |
| 2017/0246094 A1 | * | 8/2017 | Dreher ................. A61K 8/365 |
| 2018/0044550 A1 | * | 2/2018 | Arkles ................. C04B 41/009 |

FOREIGN PATENT DOCUMENTS

| | | | |
|---|---|---|---|
| WO | 2011074144 | † | 6/2011 |
| WO | 2014116560 A1 | | 7/2014 |
| WO | WO 2014/116560 | * | 7/2014 ........... C07D 207/27 |

OTHER PUBLICATIONS

Database GNPD [Online] MINTEL; Aug. 26, 2014 (Aug. 26, 2014), anonymous: "Nutri Cream," XP055694393, retrieved from www.gnpd.com, Database Accession No. 2614243 (Abstract).
Database GNPD [Online] MINTEL; Dec. 31, 2018 (Dec. 31, 2018) anonymous: "Anti-Ageing Emulsion," XP055694389, retrieved from www.gnpd.com, Database Accession No. 6230825 (Abstract).
Database GNPD [Online] MINTEL; Jul. 7, 2011 (Jul. 7, 2011), anonymous: "Anti-Wrinkle Eye Contour Cream," XP055694395, retrieved from www.gnpd.com, Database Accession No. 1585136 (Abstract).
International Preliminary Report on Patentability issued Nov. 4, 2021 in International Application No. PCT/US2020/021675.
International Search Report and Written Opinion issued May 25, 2020 in International Application No. PCT/US2020/021675.
Office Action issued Feb. 10, 2021 in U.S. Appl. No. 16/812,700, by Arkles.
Office Action issued Jun. 15, 2021 in U.S. Appl. No. 16/812,700, by Arkles.
Weathersby et al., "Brazilian keratin hair treatment: a review," Journal of Cosmetic Dermatology, vol. 12, pp. 144-148 (2013).
Office Action issued Nov. 23, 22 in CA Application No. 3137062.
Office Action issued Dec. 19, 22 in JP Application No. 2021-563094.
Office Action issued Oct. 24, 2023 in KR 10-2021-7038015.
Office Action issued May 14, 2024 in EP Application No. 20716064.9.
Office Action issued Jun. 26, 2024 in KR Application No. 10-2021-7038015.
Office Action issued Jun. 28, 2024 in CA Application No. 3137062.

* cited by examiner
† cited by third party

*Primary Examiner* — Anna R Falkowitz
(74) *Attorney, Agent, or Firm* — Panitch Schwarze Belisario & Nadel LLP

(57) ABSTRACT

Compositions and methods for reshaping keratin-rich substrates while forming adherent flexible films contain emulsified or soluble mixtures of silanols and hemiaminals or the reaction products of silanols and hemiaminals including silylated hemiaminals. A method for treating split-ends in hair is also described.

10 Claims, No Drawings

COMPOSITIONS AND METHODS FOR RESHAPING KERATIN-RICH SUBSTRATES AND FORMING ADHERENT FLEXIBLE FILMS

CROSS-REFERENCE TO RELATED APPLICATION

This application is a divisional of co-pending U.S. patent application Ser. No. 16/812,700, filed Mar. 9, 2020, which claims priority to U.S. provisional patent application No. 62/838,691, filed Apr. 25, 2019, the disclosures of which are herein incorporated by reference in their entirety.

BACKGROUND OF THE INVENTION

It is often desirable to reshape or relax keratin-rich substrates, such as wool, silk, and hair, while simultaneously imparting a soft feel, also described as "hand," or a smooth tactile response to the modified substrate. Gloss or sheen of the treated substrate is an additional desirable feature. A common method of modifying keratin-rich substrates is to apply treatments containing formaldehyde (see, for example, C. Wethersby et al. *Journal of Cosmetic Dermatology*, 12, 144-148 (2013)) or glyoxal (see U.S. Pat. No. 3,951,156). However, neither of these methods smooths the hair or provides gloss. Further, formaldehyde is toxic and a possible carcinogen, and an alternate method of providing hair relaxation for consumers without formaldehyde would reduce health risk. Methods for softening and conditioning fibers, hair, and skin using imidazolinium compounds are also known (see U.S. Pat. No. 4,720,383)

Hemiaminal ethers (also referred to as "aminals") are a class of ethers having the general structure R'''—C(NR'$_2$)(OR'')—R''''. Hemiaminal ethers may be linear or cyclic; glycosylamines are examples of cyclic hemiaminal ethers. Hemiaminal ethers may be derived from aldehydes, as shown in the structure to the left below, or from ketones, as shown in the structure to the right below.

Compounds having multiple hemiaminal substituents include imidazolidinyl urea, diazolidinyl urea (both shown below), and polyoxymethylene urea.

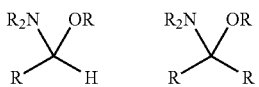

Imidazolidinyl urea

Diazolidinyl urea

SUMMARY OF THE INVENTION

A composition according to one embodiment of the disclosure comprises at least one organosilanol component and at least one organic hemiaminal component.

In a second embodiment, the disclosure is directed to a kit comprising a substrate-activating component, a mixture comprising at least one silanol and at least one siloxane, and at least one organic hemiaminal.

A method for reshaping a keratin-rich substrate according to a further embodiment of the disclosure comprises:
(a) applying a substrate-activating composition to the substrate;
(b) warming and drying the substrate;
(c) applying a fixative composition to the substrate; and
(d) warming and drying the substrate;
wherein the fixative composition comprises a mixture comprising at least one silanol and at least one siloxane, and at least one organic hemiaminal; and
wherein the substrate-activating component is an aqueous solution having a pH of about 1 to 4 or a pH of about 10 to 13.

A method for treating split-ends in hair according to a further embodiment of the disclosure comprises:
(a) applying a substrate-activating composition to the hair;
(b) warming and drying the hair;
(c) applying a fixative composition to the hair; and
(d) warming and drying the hair;
wherein the fixative composition comprises a mixture comprising at least one silanol and at least one siloxane, and at least one organic hemiaminal; and
wherein the substrate-activating component is an aqueous solution having a pH of about 1 to 4 or a pH of about 10 to 13.

DETAILED DESCRIPTION OF THE INVENTION

The disclosure relates to compositions which impart a smooth feel and a soft tactile interaction to a substrate by modifying the substrate to provide it with a durable, wash-resistant soft drape behavior. Additionally, the compositions create a flexible film that conforms to keratin-rich substrates, such as wool or hair. These compositions are particularly attractive as hair treatment products because they are free of toxic formaldehyde. The disclosure also relates to a method for providing a keratin-rich substrate with a wash-resistant smooth film with gloss and reshaping the substrate while maintaining its strength and durability. Application of the compositions described herein to hair consolidates frayed and damaged hair and acts to repair "split-ends." Finally, the disclosure provides a method of getting formaldehyde which may be formed during substrate processing.

The term "keratin-rich" refers to a substrate containing about 75 mass % or more keratin on a dry basis. Keratin-rich substrates include, but are not limited to, silk, wool and hair.

The compositions according to aspects of the disclosure are aqueous mixtures of two components: an organosilanol component (monomeric, polymeric or resinous) and an organic hemiaminal component (such as a hemiaminal ether, a hemiaminal silyl ether, and/or a hemiacetal silyl ether). Together, these components can methylolate (derivatize a protic species with an O—(CH$_2$O)— group) or crosslink by forming bridged acetal bonds O—(C(OH)HCH(OH)O)— with keratin substrates and form flexible films that encapsulate the substrates.

The silanol component of the composition is not particularly limited and may be any monomeric, polymeric, or resinous silanol, or combinations thereof. For example, exemplary polymeric silanols are polymeric diorganosiloxanes in which there is a hydroxyl group bonded to a silicon atom, which could also be described as hydroxy-terminated polydiorganosiloxanes such as hydroxy-terminated polydimethylsiloxane.

Organosilanetriols (which contain three hydroxyl groups bound to a silicon atom) are preferred monomeric silanol components because they have a greater ability than monosilanol or disilanol compounds to form silylated hemiaminals and silylated acetals with film forming properties. Examples of preferred organosilanetriols include, but are not limited to, alkylsilanetriols such as propylsilanetriol and octylsilanetriol and their oligomeric condensation products, aromatic silanetriols, such as phenylsilanetriol, in the form of emulsions, and methoxy(diethyleneoxy)propyl-silanetriol in solution form. It is also within the scope of the disclosure to include in the composition diorganosilanediols including dialkylsilanediols, such as di-n-butylsilanediol, trimethylsilanol, and/or phenyldimethylsilanol, either alone or in combination with other organosilanols. Preferred organosilanetriols and diorganosiloxanes are described in U.S. Patent Application Publication No. 2018/0044550, the disclosure of which is herein incorporated by reference in its entirety. Appropriate resinous silanols include, for example, silanol-terminated "T" resins which are also referred to as silanol-terminated polysilsesquioxanes.

The hemiaminal compound of the composition may be any water-soluble or water-dispersible organic hemiaminal such as a hemiaminal ether, a hemiaminal silyl ether, and/or a hemiacetal silyl ether, but compounds having multiple hemiaminal substituents are most preferred, including, but not limited to, imidazolidinyl urea, diazolidinyl urea, and polyoxymethylene urea. Hemiaminal silyl ethers or hemiacetal silyl ethers may be included in the composition as distinct components or may be formed by the reaction of hemiaminals with silanol-containing compounds. Examples of preferred silylated hemiaminals (hemiaminal silyl ethers) include the following:

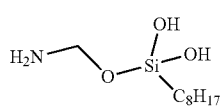

Octyl(dihydroxy)siloxyaminal

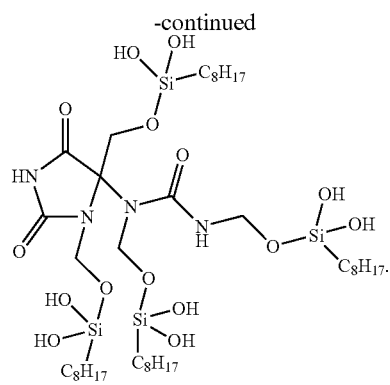

tetrakis(octyl(dihydroxy)silyloxy)diazolidinylurea

Water soluble or water-dispersible hemiaminal ethers may be formed in the presence of the silanol species, leading directly to the silylated hemiaminals, by mixing solutions of urea and formalin with solutions or emulsions of the silanol species. However, this is not a preferred method for forming the compositions according to the disclosure because traces of unreacted formaldehyde may remain.

Hemiaminal silyl ether and hemiacetal silyl ether have the general formulas RNH—CH$_2$—O—Si(OR$_{3-n}$)R'$_n$ and RO—CH$_2$—OSi(OR$_{3-n}$)R'$_n$, where R is a silicon or hydrogen atom or an organic group and R' is an organic group.

While not wishing to be bound by theory, it is believed that organosilanols form hemiacetal silyl ethers by reaction with hemiaminal ethers, initially forming hemiaminal silyl ethers. The hemiacetal silyl ethers are expected to have greater stability than hemiacetals because the acidity of the silanol group (SiO—H) is relatively greater than the corresponding alcohol (CO—H). Further, due to the greater stability, dissociation of the hemiacetals to formaldehyde as a consequence of the aqueous interaction is suppressed. Most importantly, the hemiacetal silyl ethers are more effective in methylolating keratin-rich substrates in aqueous media than formaldehyde. While silyl ethers of other aldehydes such as glyoxal and glutaraldehyde can form compositions of this disclosure, they are not preferred.

The compositions of the disclosure are activated by acidic pH (via addition of organic acids such as maleic acid or maleic acid, monoethyl ester) or by basic pH greater than 10 (via addition of a base such as sodium hydroxide).

In one embodiment, the active components of the compositions are provided as two or three component kits, in which one or more of the components are provided separately and are mixed or activated immediately prior to use. One component (Part A) of a preferred kit according to the disclosure is a substrate activating component comprising an aqueous solution containing maleic acid or a maleate salt or, alternatively, an aqueous solution adjusted to a pH of about 10 to 13. Part B is a fixative component of the kit and is provided as a composition containing a silanol/siloxane mixture such as described in U.S. Pat. No. 10,487,242 No. 2018/0044550, additionally containing an organic hemiaminal component (hemiaminal ether, hemiaminal silyl ether, and/or hemiacetal silyl ether as described above). The fixative component B may be used at 100% concentration but is preferably in aqueous solution at a concentration of about 1 to 30%. Alternatively, the silanol/siloxane mixture and the hemiaminal component may be provided as separate components in a three-component kit and the solutions combined prior to use.

A method for reshaping a keratin-rich substrate according to the disclosure involves first applying a substrate activating composition (also referred to as "Part A") which includes a pH adjusted aqueous solution to the substrate, then gradually warming and drying the substrate. A further step involves the application of a fixative composition as described above (also referred to as "Part B") to the substrate as a pH adjusted aqueous solution or dispersion at room temperature, then gradually warming and drying the substrate. Alternatively, Part B may be applied to the substrate while it is being gradually warmed and dried (after application of Part A), then the substrate is warmed and dried again to complete the process. pH adjustment is preferably performed to a pH of about 1 to 4 or to a pH of about 10 to 13. While not wishing to be bound by theory, it is believed that adjusting the pH outside the "neutral range" of pH about 5 to 8 causes a slight denaturation of keratin, providing more accessibility to reactive hydroxyl or amine groups in the protein backbone. Part B is preferably adjusted to the same pH as part A using the same components.

A method for treating split-ends in hair according to the disclosure involves first applying a substrate activating composition (also referred to as "Part A") which includes a pH adjusted aqueous solution to the hair, then gradually warming and drying the hair. A further step involves the application of a fixative composition as described above (also referred to as "Part B") to the hair as a pH adjusted aqueous solution or dispersion at room temperature, then gradually warming and drying the hair. Alternatively, Part B may be applied to the hair while it is being gradually warmed and dried (after application of Part A), then the hair is warmed and dried again to complete the process. pH adjustment is preferably performed to a pH of about 1 to 4 or to a pH of about 10 to 13. Part B is preferably adjusted to the same pH as part A using the same components.

The appropriate time and temperature for warming and drying the substrate after the application of the compositions described above are determined by the type of substrate, and range from seconds to minutes at a maximum temperature of about 250° C. to longer periods such as about 10-30 minutes at about 90° C. Commercial wool textiles may allow process temperatures up to 250° C., while hair treatment of an individual in a home or salon environment using a flat iron is preferably at a lower temperature, for example at 180° C. to 230° C. Advantageously, the transformation of the keratin-rich substrates, including hair and wool, is maintained in successive washings.

While it is not believed that formaldehyde is formed in the compositions of the disclosure, in a preferred embodiment an amine bound to a polymeric siloxane such as aminoethylaminopropylmethoxysiloxane—dimethylsiloxane copolymer is incorporated as a precaution because it can react with any free aldehydes present by forming a Schiff base (imine).

It is within the scope of the disclosure to use the composition and method in conjunction with a known hair strengthening treatment, but this is generally not preferred.

Aspects of the disclosure will now be described in connection with the following non-limiting examples.

EXAMPLES

Example 1: Composition 1 (pH Adjusted to 11 Using Maleate)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with a dilute solution of maleic acid, trioxatridecane diamine salt, and adjusted to pH 11 with sodium hydroxide. In a general sense, the composition was a complex mixture derived from a 2.0% silanol-rich emulsion, 0.5% diazolidinyl urea, and balance water, adjusted to pH 11 with sodium hydroxide.

Example 2: Composition 2 (pH Adjusted to 11 Using Sodium Hydroxide)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with a dilute solution of sodium hydroxide having a pH of 11. In a general sense, the composition was a complex mixture derived from a 2.0% silanol-rich emulsion, 0.5% diazolidinyl urea, and balance water, adjusted to pH 11 with sodium hydroxide.

Example 3: Composition 3 (pH Adjusted to 11 Using Buffer)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with 0.35% dibasic sodium phosphate buffer having a pH of 11. In a general sense, the composition was a complex mixture derived from a 2.0% silanol-rich emulsion, 0.5% diazolidinyl urea, and balance water, adjusted to pH 11 with sodium hydroxide.

Example 4: Composition 4 (2× Higher Silicone Content in Part B)

A 3 neck flask equipped with a moderate speed (50-500rpm) stirrer was charged with 1700 mL of deionized water and 8 mL of acetic acid. 320 mL octyltriethoxysilane was added rapidly through an addition funnel. Initially the mixture formed two phases but in 3-5 hours it became a single homogeneous phase. As soon as the solution was homogeneous, 160 mL of 1M sodium bicarbonate solution was added to adjust to pH 4. After the neutralization was complete, 130 grams of a diamine functional silicone emulsion containing 50% solids, having an amine equivalent 0.45 mEq/g and sold by Wacker Silicones under the trade name BS1306 was added to the mixture with low speed (<50rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 25 parts with a dilute solution of maleic acid, trioxatridecane diamine salt and adjusted to pH of 11 with sodium hydroxide. In a general sense the composition was a complex mixture derived from a 4.0% silanol-rich emulsion and 0.5% diazolidinyl urea and balance water, adjusted to pH 11 with sodium hydroxide.

Example 5: Composition 5 (4× Higher Silicone Content in Part B)

A 3 neck flask equipped with a moderate speed (50-500rpm) stirrer was charged with 1700 mL of deionized water and 8 mL of acetic acid. 320 mL octyltriethoxysilane was added rapidly through an addition funnel. Initially the mixture formed two phases but in 3-5 hours it became a single homogeneous phase. As soon as the solution was homogeneous, 160 mL of 1M sodium bicarbonate solution was added to adjust to pH 4. After the neutralization was complete, 130 grams of a diamine functional silicone emulsion containing 50% solids, having an amine equivalent 0.45 mEq/g and sold by Wacker Silicones under the trade name BS1306 was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 4 parts to 50 parts with a dilute solution of maleic acid, trioxatridecane diamine salt and adjusted to pH of 11 with sodium hydroxide. In a general sense the composition was a complex mixture derived from 8.0% silanol-rich emulsion and 0.5% diazolidinyl urea and balance water, adjusted to pH 11 with sodium hydroxide.

Example 6: Composition 6 (Containing 1.0% Glyoxal)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) and 1 wt % of a 40% glyoxal solution in water were then added to the emulsion with agitation and agitation was continued after the addition for 5-10 minutes. Immediately prior to use, the final composition was formed by diluting the mixture 1 part to 50 parts with a dilute solution of maleic acid, trioxatridecane diamine salt, and adjusted to pH 11 with sodium hydroxide. In a general sense, the composition was a complex mixture derived from a 2.0% silanol-rich emulsion, 0.5% diazolidinyl urea, and balance water, adjusted to pH 11 with sodium hydroxide.

Example 7: Composition 7 (pH 3 Silane Solution)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 3. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with a dilute solution of maleic acid, trioxatridecane diamine salt, and adjusted to pH 11 with sodium hydroxide. In a general sense, the composition was a complex mixture derived from a 2.0% silanol-rich emulsion, 0.5% diazolidinyl urea, and balance water, adjusted to pH 11 with sodium hydroxide.

Example 8: Composition 8 (Employing pH 6 Silane Solution)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 6. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with a dilute solution of maleic acid, trioxatridecane diamine salt, and adjusted to pH 11 with sodium hydroxide. In a general sense, the composition was a complex mixture derived from a 2.0% silanol-rich emulsion, 0.5% diazolidinyl urea, and balance water, adjusted to pH 11 with sodium hydroxide.

Example 9: (Composition 9)—(8× Higher Silicone Content in part B)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially the mixture formed two phases but in 3-5 hours it became a single homogeneous phase. As soon as the solution was homogeneous, 160 mL of 1M sodium bicarbonate solution was added to adjust to pH 4. After the neutralization was complete, 130 grams of a diamine functional silicone emulsion containing 50% solids, having an amine equivalent 0.45 mEq/g and sold by Wacker Silicones under the trade name BS1306 was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 8 part to 50 parts with a dilute solution of maleic acid, trioxatridecane diamine salt and adjusted to pH of 11 with sodium hydroxide. In a general sense the composition was a complex mixture derived from 16.0% silanol-rich emulsion and 0.5% diazolidinyl urea and balance water, adjusted to pH 11 with sodium hydroxide.

Example 10: Composition 10 (Containing 4.0% Glyoxal)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) and 4.0% of a 40% glyoxal solution in water were then added to the emulsion with agitation and agitation was continued after the addition for 5-10 minutes. Immediately prior to use, the final composition was formed by diluting the mixture 1 part to 50 parts with a dilute solution of maleic acid, trioxatridecane diamine salt, and adjusted to pH 11 with sodium hydroxide. In a general sense, the composition was a complex mixture derived from a 2.0% silanol-rich emulsion, 0.5% diazolidinyl urea, and balance water, adjusted to pH 11 with sodium hydroxide.

Example 11: Composition 11 (2% Diazolidinyl Urea)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 3. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (24.0 g) was then added to the emulsion with agitation and agitation was continued after the addition for 5-10 minutes. Immediately prior to use, the final composition was formed by diluting the mixture 1 part to 50 parts with a dilute solution of maleic acid, trioxatridecane diamine salt, and adjusted to pH 11 with sodium hydroxide. In a general sense, the composition was a complex mixture derived from a 2.0% silanol-rich emulsion, 1.0% diazolidinyl urea, and balance water, adjusted to pH 11 with sodium hydroxide.

Example 12: Composition 12 (pH 4 Using Maleic Acid)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with a solution prepared by dissolving 0.152 g maleic anhydride in 1L water. In a general sense, the composition was a complex mixture derived from a 2.0% silanol-rich emulsion, 0.5% diazolidinyl urea, and 0.02% maleic anhydride solution in water with pH <4.

Example 13: Composition 13 (pH 11 Using Amine)

A 3 neck flask equipped with a moderate speed (50-500 rpm) stirrer was charged with 1700 mL of deionized water and 8 mL of acetic acid. 320 mL octyltriethoxysilane was added rapidly through an addition funnel. Initially, the mixture formed two phases but in 3-5 hours it became a single homogeneous phase. As soon as the solution was homogeneous, 160 mL of 1M sodium bicarbonate solution was added to adjust the solution to pH 4. After the neutralization was complete, 130 g of a diamine functional silicone emulsion containing 50% solids and having an amine equivalent 0.45 mEq/g (commercially available from Wacker Silicones under the trade name BS1306) was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 50 parts with a solution of 16.85 g polyether diamine in 1 L water. In a general sense, the composition was a complex mixture derived from a 2.0% silanol-rich emulsion, 0.5% diazolidinyl urea, and 0.02% polyether diamine solution in water with pH>11.

Example 14: Composition 14 (10× Higher Silicone Content in Part B)

A 3 neck flask equipped with a moderate speed (50-500rpm) stirrer was charged with 1700 mL of deionized water and 8 mL of acetic acid. 320 mL octyltriethoxysilane was added rapidly through an addition funnel. Initially the mixture formed two phases but in 3-5 hours it became a single homogeneous phase. As soon as the solution was homogeneous, 160 mL of 1M sodium bicarbonate solution was added to adjust to pH 4. After the neutralization was complete, 130 grams of a diamine functional silicone emulsion containing 50% solids, having an amine equivalent 0.45 mEq/g and sold by Wacker Silicones under the trade name BS1306 was added to the mixture with low speed (<50 rpm) agitation. The mixture was allowed to age at room temperature for at least 24 hours. Diazolidinyl urea (12.0 g) was then added to the emulsion with agitation and agitation was continued after the addition for 5-10 minutes. Immediately prior to use, the final composition was formed by diluting the mixture 1 part to 40 parts with a dilute solution of maleic acid, trioxatridecane diamine salt and adjusted to pH of 11 with sodium hydroxide. In a general sense the composition was a complex mixture derived from 20.0% silanol-rich emulsion and 0.5% diazolidinyl urea and balance water, adjusted to pH 11 with sodium hydroxide.

Example 15: Method of Relaxing and Smoothing Hair

Pre-washed and dried hair samples were combed or otherwise detangled. A substrate activating composition (Part A) containing a 0.25% solution of maleic acid, trioxatridecane diamine salt adjusted to pH 11 with sodium hydroxide was applied to the substrate (hair) so that all strands were completely contacted with liquid. Preferably, the solution was applied in 1 to 2 inch sections. Part A was allowed to contact the hair for 5 minutes and was then dried using heat, preferably a blow dryer using tension and a comb or brush to pull 1 to 2 inch sections of the substrate straight. After all sections were completely dry, the substrate was further straightened with four passes of a flat iron set to 190° C. The substrate was allowed to rest (left untouched) for 5 minutes, or until not warm to the touch. In the second stage of treatment, the hair was contacted with the composition of part B. Part B is a composition as described in Examples 1 to 13 above and contains the same concentration of maleic acid, trioxatridecane diamine salt and sodium hydroxide as part A. After application of Part B, the hair was immediately dried, preferably in tension, for example with heat from a blow dryer while combing or brushing 1 to 2 inch sections of hair. After all sections were completely dry, the hair was further straightened with four passes of a flat iron set to 190° C. The hair was not washed immediately after treatment. The hair was qualitatively observed to be relaxed and smoother with enhanced shine after the treatment. The relaxation and smoothness were maintained after 25 successive washings of the hair.

Example 16: Method of Relaxing and Smoothing Hair

The method described in Example 15 was repeated, except that the flat iron temperature was adjusted to 230° C.

Example 17: Method of Relaxing and Smoothing Hair

Pre-washed and dried hair samples were combed or otherwise detangled. The composition of part A as described in Example 15 was applied to the substrate (hair) so that all strands were completely contacted with liquid. Preferably, the solution was applied in 1 to 2 inch sections. Part A was allowed to contact the hair for 5 minutes. In the second stage of treatment, the hair was contacted with the composition of part B as described above in Example 15. After application of Part B, the hair was immediately dried, preferably in tension, for example with heat from a blow dryer while combing or brushing 1 to 2 inch sections of hair. After all sections were completely dry, the hair was further straightened with four passes of a flat iron set to 190° C. The hair was not washed immediately after treatment. The hair qualitatively was relaxed and smoother with enhanced shine after the treatment.

When applied using the method described in Example 15, the compositions prepared in Examples 1 to 13 resulted in different amounts of smoothing and relaxing. In general, smoothing and relaxing follow the same trend, with formulations containing maleate and higher concentrations of silicone emulsion performing better than formulations lacking those components. Smoothing is improved with higher concentrations of silicone emulsion, while relaxing is approximately equal.

Example 18: Method of Relaxing and Smoothing Hair (Shortened Version by Omitting Straightening Step after Drying Part B)

Pre-washed and dried hair samples were combed or otherwise detangled. A substrate activating composition (Part A) containing a 0.25% solution of maleic acid, trioxatridecane diamine salt adjusted to pH 11 with sodium hydroxide was applied to the substrate (hair) so that all strands were completely contacted with liquid. Preferably, the solution was applied in 1 to 2 inch sections. Part A was allowed to contact the hair for 5 minutes and was then dried using heat, preferably a blow dryer using tension and a comb or brush to pull 1 to 2 inch sections of the hair straight. After all sections were completely dry, the hair was further straightened with four passes of a flat iron set to 190° C. The hair was allowed to rest (left untouched) for 5 minutes, or until not warm to the touch. In the second stage of treatment, the hair was contacted with the composition of part B. Part B is a composition as described in Examples 1 to 14 above and contains the same concentration of maleic acid, trioxatridecane diamine salt and sodium hydroxide as part A. After application of Part B, the hair was immediately dried, preferably in tension, for example with heat from a blow dryer while combing or brushing 1 to 2 inch sections of hair. The hair was washed immediately after treatment. The hair was qualitatively observed to be relaxed and smoother with enhanced shine after the treatment. The relaxation and smoothness were maintained after 25 successive washings of the hair.

Example 19: Method of Relaxing and Smoothing Hair (Shortened Version by Applying Part A to Damp Hair and Omitting Straightening Step after Drying Part B)

Pre-washed and >50% dried hair samples were combed or otherwise detangled. A substrate activating composition (Part A) containing a 0.25% solution of maleic acid, trioxatridecane diamine salt adjusted to pH 11 with sodium hydroxide was applied to the substrate (hair) so that all strands were completely contacted with liquid. Preferably, the solution was applied in 1 to 2 inch sections. Part A was allowed to contact the hair for 5 minutes and was then dried using heat, preferably a blow dryer using tension and a comb or brush to pull 1 to 2 inch sections of the hair straight. After all sections were completely dry, the hair was further straightened with four passes of a flat iron set to 190° C. The hair was allowed to rest (left untouched) for 5 minutes, or until not warm to the touch. In the second stage of treatment, the hair was contacted with the composition of part B. Part B is a composition as described in Examples 1 to 14 above and contains the same concentration of maleic acid, trioxatridecane diamine salt and sodium hydroxide as part A. After application of Part B, the hair was immediately dried, preferably in tension, for example with heat from a blow dryer while combing or brushing 1 to 2 inch sections of hair. The hair was washed immediately after treatment. The hair was qualitatively observed to be relaxed and smoother with enhanced shine after the treatment. The relaxation and smoothness were maintained after 25 successive washings of the hair.

Example 20: Method of Treating Split Ends in Hair

Pre-washed and >50% dried hair samples were combed or otherwise detangled. A substrate activating composition (Part A) containing a 0.25% solution of maleic acid, trioxatridecane diamine salt adjusted to pH 11 with sodium hydroxide was applied to the bottom 2-3 inches of the substrate (hair) so that all strands were completely contacted with liquid. Part A was allowed to contact the hair for 5 minutes and was then dried using heat, preferably a blow dryer using tension and a comb or brush to pull the substrate straight. After all sections were completely dry, the hair was further straightened with four passes of a flat iron set to 190° C. The hair was allowed to rest (left untouched) for 5 minutes, or until not warm to the touch. In the second stage of treatment, the same bottom 2-3 inches of the hair was contacted with the composition of part B. Part B is a composition as described in Examples 1 to 14 above and contains the same concentration of maleic acid, trioxatridecane diamine salt and sodium hydroxide as part A. After application of Part B, the hair was immediately dried, preferably in tension, for example with heat from a blow dryer while combing or brushing 1 to 2 inch sections of hair. The hair was washed immediately after treatment. External laboratory testing of 50 hair samples resulted in 74% of split ends completely repaired and an additional 14% of split ends mended. Mending split ends is defined as reducing the angle of the split ends by at least 30%. The hair was qualitatively observed to be stronger after the treatment.

It will be appreciated by those skilled in the art that changes could be made to the embodiment described above without departing from the broad inventive concepts thereof. Also, based on this disclosure, a person of ordinary skill in the art would further recognize that the relative proportions of the components illustrated above could be varied without departing from the spirit and scope of the invention. It is understood, therefor, that this invention is not limited to that particular embodiment disclosed, but it is intended to cover modifications within the spirit and scope of the present invention as defined by the appended claims.

We claim:

1. A kit comprising of a substrate-activating component, a mixture comprising at least one silanol and at least one siloxane, and at least one organic hemiaminal, wherein the substrate-activating component is an aqueous solution having a pH of about 10 to 13.

2. The kit according to claim 1, wherein the at least one organic hemiaminal is selected from the group consisting of a hemiaminal ether, a hemiaminal silyl ether, and a hemiacetal silyl ether.

3. The kit according to claim 1, wherein when the mixture comprising at least one silanol and at least one siloxane is combined with the at least one organic hemiaminal, the at least one silanol and the at least one organic hemiaminal react to form a silylated hemiaminal without formation of formaldehyde.

4. The kit according to claim 1, wherein the at least one silanol is a monomeric, polymeric, or resinous organosilanol.

5. The kit according to claim 1, wherein the at least one silanol is a hydroxy-terminated polymeric diorganosiloxane.

6. The kit according to claim 1, wherein the at least one silanol is an organosilanetriol or diorganosilanediol.

7. The kit according to claim 1, wherein the at least one organic hemiaminal is selected from the group consisting of a memiaminal ether, a hemiaminal silyl ether, and a hemiacetal silyl ether.

8. The composition according to claim 7, wherein the at least one organic hemiaminal is selected from the group consisting of imidazolidinyl urea, diazolidinyl urea, and polyoxymethylene urea.

9. A kit consisting of a substrate-activating component, a mixture comprising at least one silanol and at least one siloxane, at least one organic hemiaminal, and an amine bound to a polymeric siloxane, wherein the substrate-activating component is an aqueous solution having a pH of about 10 to 13.

10. The kit according to claim 1, wherein the at least one silanol component comprises an organosilanetriol and a diorganosiloxane.

* * * * *